United States Patent [19]

Gmeinder

[11] 4,149,094
[45] Apr. 10, 1979

[54] DENTAL APPARATUS HAVING A PLURALITY OF DENTAL INSTRUMENTS

[75] Inventor: Hermann Gmeinder, Biberach, Fed. Rep. of Germany

[73] Assignee: Kaltenbach & Voigt GmbH & Co., Biberach, Fed. Rep. of Germany

[21] Appl. No.: 820,025

[22] Filed: Jul. 28, 1977

[30] Foreign Application Priority Data

Aug. 17, 1976 [DE] Fed. Rep. of Germany ....... 2636957

[51] Int. Cl.$^2$ ............................................. H02J 13/00
[52] U.S. Cl. ..................... 307/12; 307/203; 32/22; 307/149
[58] Field of Search ....................... 307/11, 29, 38, 51, 307/115, 102, 150, 203, 241, 242; 32/22, 23; 128/303.13, 303.14, 303.17

[56] References Cited

U.S. PATENT DOCUMENTS 3,702,940  11/1972  Stewart ................................. 32/22

Primary Examiner—L. T. Hix
Assistant Examiner—S. D. Schreyer

Attorney, Agent, or Firm—Haseltine, Lake & Waters

[57] ABSTRACT

Dental apparatus having a plurality of dental instruments, holders for the instruments, signal transmitters each operable to transmit an extraction signal when an instrument is extracted from its holder, and a logic-actuation circuit for each instrument connected to a respective signal transmitter and to all the other logic-actuation circuits. Each actuation circuit can generate an actuation signal for its associated instrument, and a blocking signal for supply to the other actuation circuits, when an extraction signal is transmitted and when no blocking signal is supplied by any of the other actuation circuits. A single connecting line interconnects the actuation circuits to transmit blocking signals therebetween, and logic identification circuits associated with the actuation circuits are each connected to the connecting line and to an input and to an output of the associated actuation circuit. Each identification circuit is operable to transmit, to the input of its associated actuation circuit, a blocking signal which may be present in the connecting line when an actuating signal is absent from the output of the actuation circuit.

4 Claims, 5 Drawing Figures

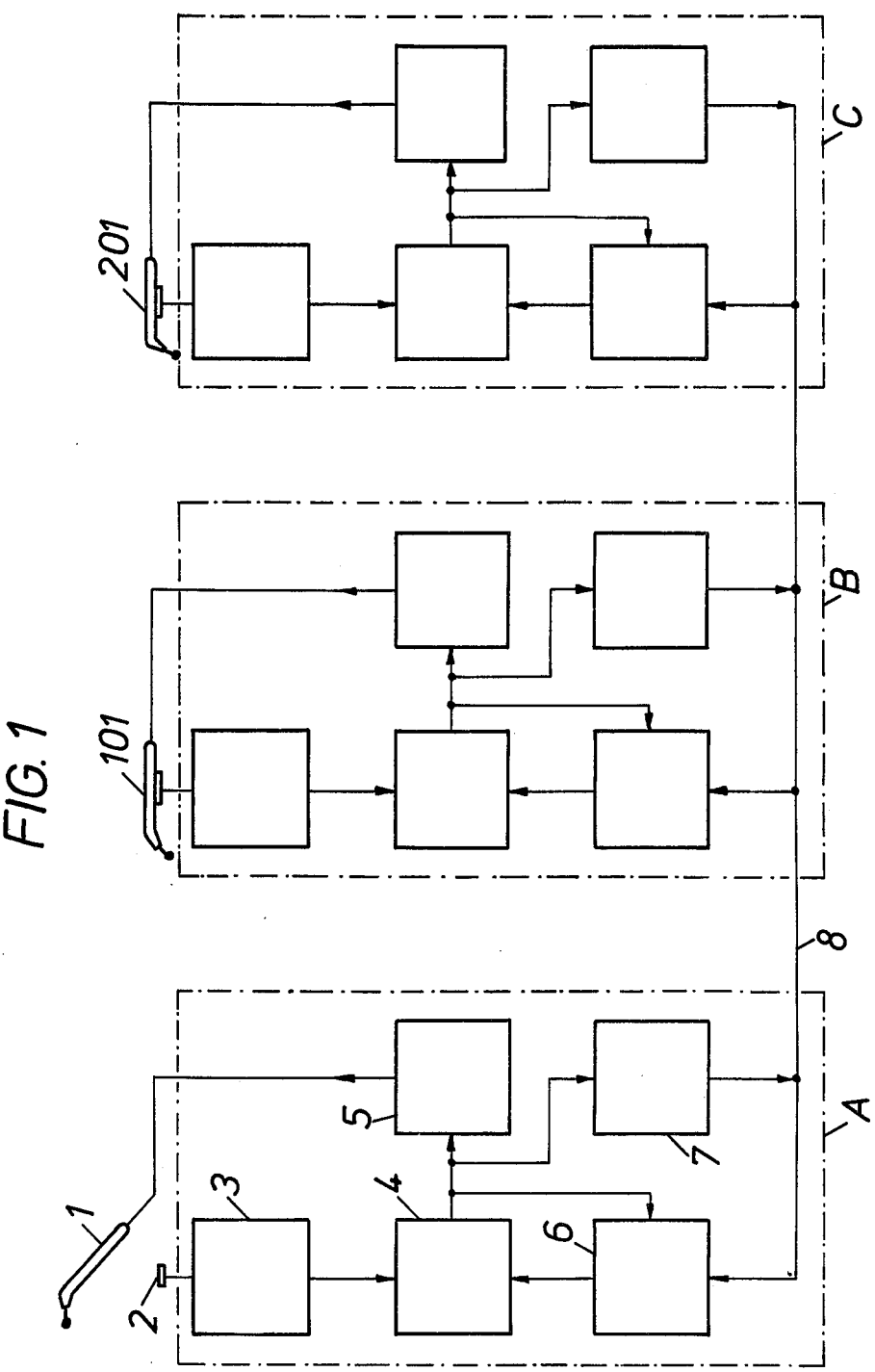

DENTAL APPARATUS HAVING A PLURALITY OF DENTAL INSTRUMENTS

BACKGROUND OF THE INVENTION

This invention relates to a dental apparatus having a plurality of instruments, holding means for said instruments, an extraction signal transmitter for each instrument operable to transmit an extraction signal when an instrument is extracted from its holding means, and a logic-actuation circuit for each instrument which is connected with the respective signal transmitter and also with the actuation circuits for the other instruments, each actuation circuit being operable to generate an actuation signal for the associated instrument and also to supply a blocking signal for the other actuation circuits when an extraction signal is transmitted from the associated signal transmitter and when no blocking signal from the other actuation circuits is present.

A dental apparatus of the above type is known from German Pat. specification No. 2 231 735. In the case of this known dental apparatus, the actuation circuits are connected with each other by a number of connecting lines which is equal to the number of instruments or actuating circuits. Each actuation circuit has a number of inputs equal to the number of instruments, one input being connected with the extraction signal transmitter and the remaining inputs with the connecting lines which transfer the blocking signal from the other actuation circuits. It is obvious that in the case of a relatively large number of instruments, with this design, a considerable outlay of components and space is necessary. Additionally, the outlay for assembly is considerable.

SUMMARY OF THE INVENTION

It is an object of the invention to so design a dental apparatus of the above type that the circuit and assembly outlay is reduced.

According to the invention there is provided dental apparatus comprising:
 a plurality of dental instruments;
 holding means for said instruments;
 a signal transmitter associated with each instrument and operable upon extraction of the respective instrument from its holding means to transmit an extraction signal;
 a logic circuit associated with each instrument and connected to the signal transmitter associated with the respective instrument, and connected to the logic circuits associated with the other instruments, each logic circuit being operable to generate an actuation signal for the respective instrument and a blocking signal for supply to the other logic circuits when an extraction signal is transmitted in respect of the respective instrument and when no blocking signal is supplied by any of the other logic circuits;
 a single connecting line connected to said logic circuits for transmitting blocking signals therebetween;
 and a logic identification circuit associated with each logic circuit, each logic identification circuit being connected to said connecting line and to an input and to an output of the associated logic circuit, and each logic identification circuit being operable to transmit a blocking signal which may be present in the connecting line to the input of the associated logic circuit when an actuating signal is absent from the output of the logic circuit.

The use of a single connecting line guarantees, in the sense of the underlying problem, a considerable reduction of the circuit and assembly outlay. With the use of only a single connecting line, however, the following problem arises: the input of each actuation circuit is connected with the connecting line so as to take up the blocking signals of other actuation circuits. Additionally, however, also the output of each actuation circuit is connected with the connecting line so as to transmit blocking signals generated by the actuation circuit to the other actuation circuits. If, then, an actuation circuit itself generates a blocking signal and if no supplementary measures were to be taken, then the actuation circuit would be obliged to block itself due to the blocking signal transmitted to its input from its output and via the single connecting line. However, this problem is solved by arranging the logic identification or realisation circuit so that no blocking signal is transmitted to the input of the actuation circuit when the logic identification circuit ascertains that the blocking signal has been generated by the actuation circuit itself. It can ascertain this due to the fact that it is connected both with the connecting line and also with the output of the actuation circuit. At this point, it should be pointed out that the outputs of the actuation circuits (as already in the state of the art) are not directly connected with the connecting line but there is connected there between also a separating element (one-way transmission means) which transmits the actuation signal directly or in varied form as blocking signal to the connecting line. The two inputs of the logic identification circuit do not therefore have the same signal supplied to them in every case.

According to a preferred arrangement, the output of each actuation circuit is connected with the connecting line by in each particular instance a single-way transmission circuit transmitting only in the direction of the connecting line and which in this case constitutes the separating element. Such a one-way transmission circuit can be produced by specially small expenditure as to circuitry. If the arrangement is of electrical design, it may consist for example of a simple diode.

In a practical embodiment of the invention, each actuation circuit comprises a NAND element one input of which is connected with the extraction signal transmitter; the realisation (logic identification) circuit comprises a further NAND element and an inverter, the input of the inverter being connected with the connecting line and the output thereof with the input of the further NAND element; the other input of the further NAND element is connected with the output of the first-mentioned NAND element; the output of the further NAND element is connected with the other input of the first-mentioned NAND element; and the one-way transmission circuit is connected with the output of the first-mentioned NAND element.

The blocking circuit can be produced both in electrical, pneumatic or hydraulic form. The reference numerals employed for the individual circuit elements are to apply to all three possibilities.

BRIEF DESCRIPTION OF THE DRAWINGS

FIG. 1 is a block circuit diagram of a dental apparatus having three dental instruments and associated circuit elements;

DESCRIPTION OF PREFERRED EMBODIMENTS

Figure 2A:
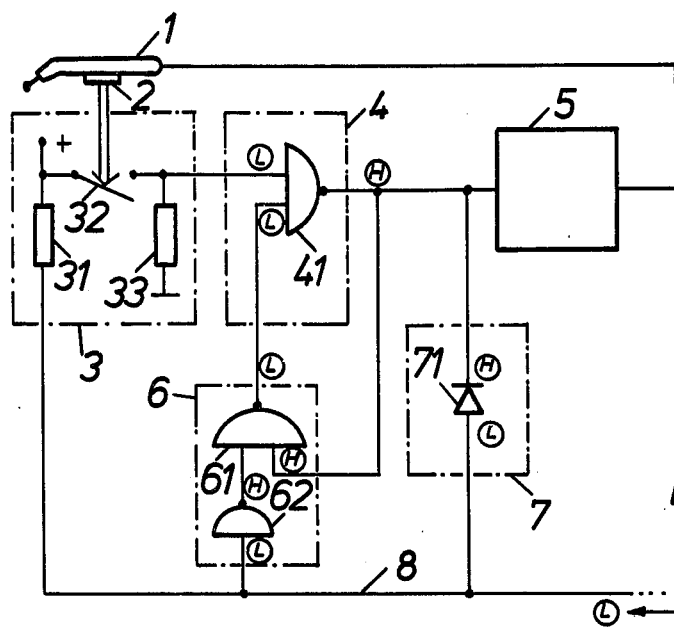
FIGS. 2a and 2b are detail circuit diagrams of a circuit element associated with a dental instrument, it being shown that the instrument does not commence to operate if there is present a blocking signal from an actuation circuit of another instrument.

Referring to FIG. 1, for the sake of simplicity only three instruments 1, 101, 201 are shown. Associated with each instrument is one of the circuit elements A, B, C. For the sake of simplicity, only the circuit element A is explained. The circuit elements B and C are correspondingly designed.

For the instrument 1, there is provided at the dental device holding or depositing means 2 connected with an extraction signal transmitter 3. The latter supplies to an input of a logic activation circuit 4 an extraction signal when the instrument 1 is extracted from the depositing means 2. The activation circuit 4 has a further input connected with the output of a logic identification circuit 6. The identification circuit 6 has two inputs of which one is connected with a connecting line 8 and the other with the output of the activation circuit 4.

The activation circuit 4 generates at its output an activation signal for an energy supply circuit 5 when there is supplied to it from the extraction signal transmitter 3 an extraction signal and when no blocking signal is supplied to it from the identification circuit 6. The activation signal generated by the activation circuit 4 is simultaneously fed to the connecting line 8 via a one-way transmission circuit 7, as a blocking signal. The connecting line 8 transmits this blocking signal to the other circuit elements B and C. When there is an activation signal at the input of the energy supply circuit 5, this supplies the instrument 1 with the necessary energy for starting-up.

It is the task of the identification circuit 6 to prevent the activation circuit 4 from being blocked by the blocking signal which it itself has generated. Since the identification circuit 6 is, apart from its connection with the input of the connecting line 8, also connected with the output of the activation circuit 4, it is able to make the logical decision as to whether the blocking signal is generated by the activation circuit 4 itself or by another activation circuit.

The identification circuit 6 operates as follows: If there is a blocking signal on the connecting line 8 prior to extraction of the instrument 1 out of the depositing means 2, then the identification circuit 6 reports the presence of this blocking signal to the activation circuit 4. Thereby, the activation circuit 4 is not able to generate an activation signal when the instrument 1 is extracted from the deposit means 2.

If, prior to extraction of the instrument 1 out of the depositing means 2 there is no blocking signal on the connecting line 8, then the identification circuit reports this condition to the activation circuit 4. If, then, the instrument 1 is extracted from the depositing means, the activation circuit 4 receives an extraction signal and correspondingly generates an activation signal. This is transferred via the one-way transmission circuit 7 to the connecting line 8, as blocking signal. However, the identification circuit 6 learns, via its input connected with the output of the activation circuit 4, that the blocking signal has been generated by the activation circuit 4. Thus, in this case it does not report the presence of a blocking signal to the connecting line 8 to the activation circuit 4, so that the activation circuit continues to generate the activation signal and the instrument 1 is able to operate further.

FIG. 2a shows an electrical realisation of the circuit. The extraction signal transmitter 3 has a resistor 31 one connection of which is at a positive voltage potential. The other connection of the resistor 31 is connected with the connecting line 8. At the connection connected with the positive voltage potential of the resistor 31 there is also one switching contact of an on-off switch 32. The other switching contact of this switch 32 is connected with a connection of a resistor 33 the other connection of which is connected to earth. The switch 32 is pressed by the depositing means 2 into the open position when the instrument 1 is in the depositing means. When the instrument 1 is extracted from the depositing means 2, then the switch 32 closes.

The activation circuit 4 comprises a NAND element 41 one input of which is connected with the connection of the resistor 33 which is not connected to earth.

The identification circuit comprises a further NAND element 61 and an inverter 62. The output of the NAND element 61 is connected with the other input of the NAND element 41. One of the inputs of the NAND element 61 is connected with the output of the NAND element 41. The other input of the NAND element 61 is connected with the output of the inverter 62 the input of which is connected to the connecting line 8. The one-way transmission circuit 7 is constituted by a diode 71 the cathode of which is connected with the output of the NAND element 41.

Figure 2B:
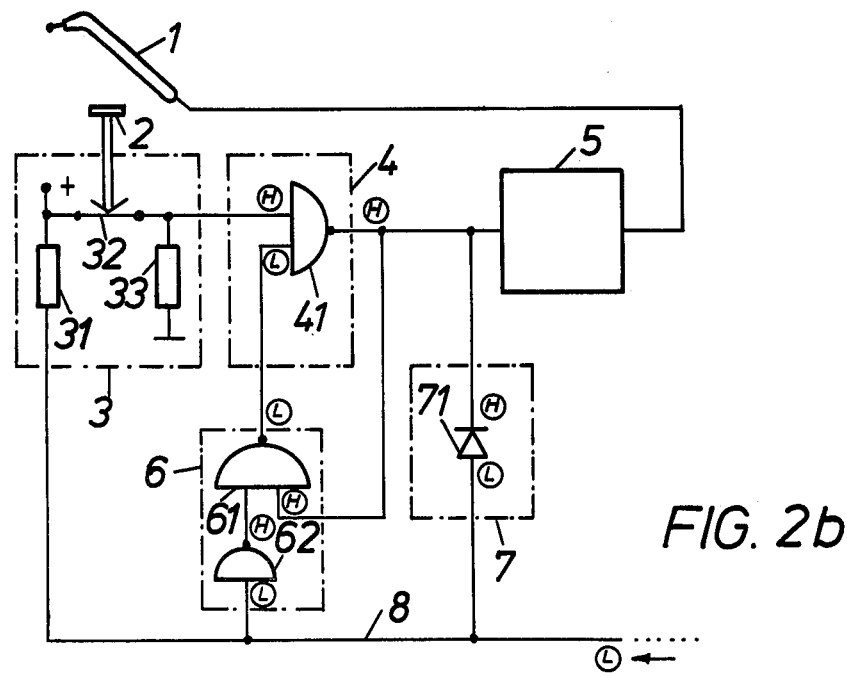

With reference to FIGS. 2a and 2b, there will hereinbelow be described the case whereby a blocking signal is present on the connecting line 8 and correspondingly the instrument 1 is not able to start up. For explanation it may be stated furthermore that the logic conditions here are designated H (high) and L (low). If H and L impinge on each other, then L will overcome H.

The NAND elements 41 and 61 generate L at their output only when H is present at both inputs, otherwise the NAND elements always generate H.

An activation signal is then to be generated by the activation circuit 4 when at the output of the activation circuit 4 L appears. The activation signal is in the present case simultaneously employed as blocking signal. Consequently, there is a blocking signal on the connecting line 8 when the logic voltage condition on this line is L.

FIG. 2a will now be considered. On connecting line 8 there is a blocking signal, i.e. the logic voltage condition on this line is L. The instrument 1 is on the depositing means 2, so that the switch 32 is open. Correspondingly, L is at one of the inputs of the NAND element 41. Thereby, at the output of the NAND element 41 only H can occur. At the input of the inverter 62, the blocking signal L occurs. Correspondingly, H appears at the output of the inverter 62. Thus H appears at both inputs of the NAND element 61. Consequently, L must be available at the output of the NAND element 61. The output condition H of the NAND element 41 means that no activation signal is generated. Since the cathode of the diode 71 is at H and the anode at L, the diode 71 does not transmit. It thus operates here as a one-way transmission circuit as much as it also does not transmit L from the connecting line 8 to the input of the energy supply circuit 5. As already mentioned, L is dominant relative to H. Transmission due to the cathode 71 is to take place only if L is present at its cathode and H at its anode.

Referring to FIG. 2b, the instrument 1 is now to be lifted off from the deposit means 2. Thereby, the switch 32 is closed and one input of the NAND element 41 receives H. The extraction signal therefore corresponds here to the logical voltage condition H. For the identification circuit 6 the conditions relative to FIG. 2a have not changed. Thus it continues to generate L for the other input of the NAND element. Correspondingly, only H can remain at the output of the NAND element 41. Thus, the instrument 1 cannot start up. The reason for this is the presence of L on the connecting line 8.

Figure 3A:
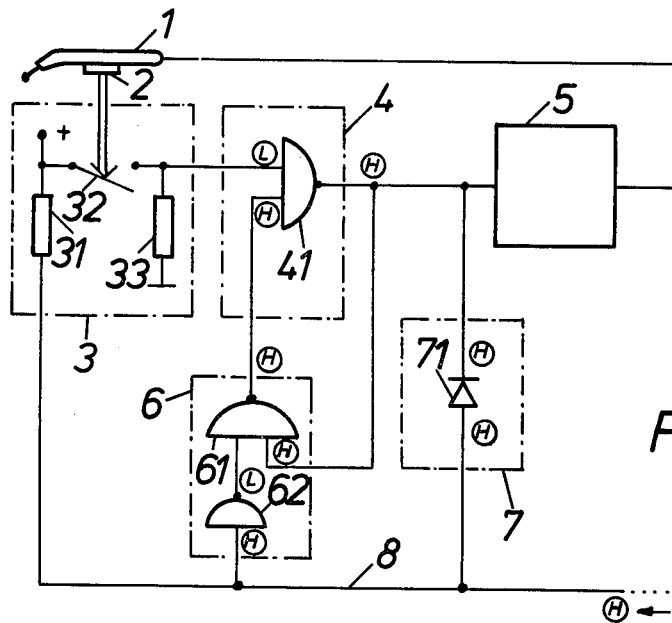
FIGS 3a and 3b are similar to FIGS. 2a and 2b, but it is shown that the instrument commences to operate when no blocking signal from the actuation circuit of another instrument is available.
Figure 3B:
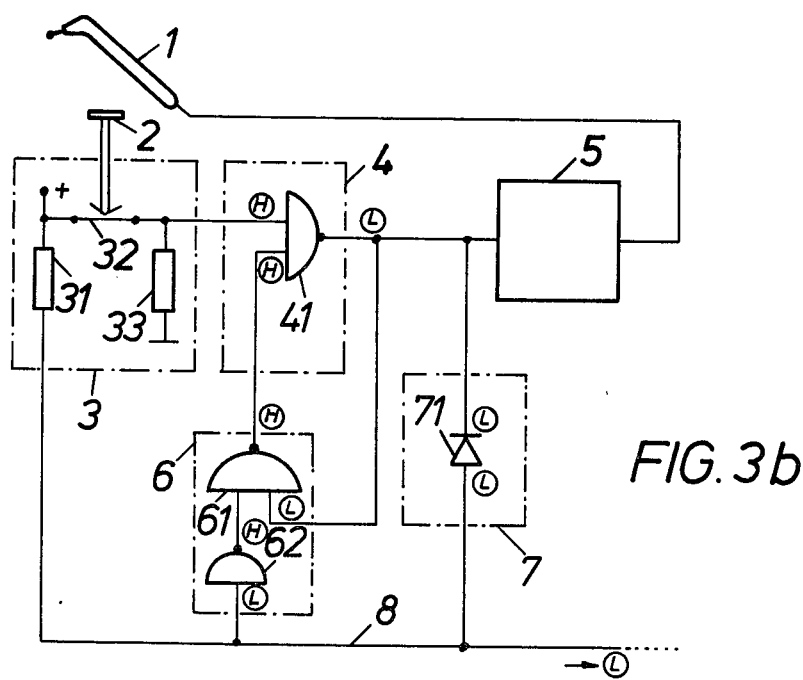

With reference to FIGS. 3a and 3b, it will now be explained that the instrument 1 is able to start up if no blocking signal is present on the connecting line 8.

Referring to FIG. 3a, the logic voltage condition of the connecting line 8 is H. The instrument 1 is on deposit 2, whereby one input of the NAND element 41 receives L. Correspondingly, only H can be generated at the output of the NAND element 41. This means that the energy supply circuit 5 has no activation signals supplied to it. Since H is present at the input of the inverter 62 H, L is generated at its output. Consequently, L and H are at the two inputs of the NAND element 61. Thus, H occurs at the output of the NAND element. H is present at the cathode and at the anode of the diode 71.

If, then, according to FIG. 3b the instrument 1 is lifted off from the deposit 2, then H is fed to the upper input of the NAND element. At the lower input of the NAND element 41 H is still present. Consequently, the NAND element 41 then generates activation signal L at its output. The energy supply circuit 5 allows the instrument 1 to start up, since L is present at the cathode of the diode 71 and initially H was present on the connecting line (see FIG. 3a), the diode 71 becomes conductive. Consequently it transmits the activation signal L as blocking signal to the connecting line. The voltage condition of the connecting line 8 thus changes from H to L. The L is present also at the input of the inverter 62 which correspondingly produces H at its output. Since, however, L is present at the input of the NAND element 61 connected with the output of the NAND element 41, the logic voltage condition at the output of the NAND element 61 remains unchanged relative to that in FIG. 3a, i.e. at H. This means that the NAND element 41 continues to generate L at its output and consequently the instrument 1 is able to continue to operate.

I claim:
1. Dental apparatus comprising:
a plurality of dental instruments;
holding means for said instruments;
a signal transmitter associated with each instrument and operable upon extraction of the respective instrument from its holding means to transmit an extraction signal;
a logic circuit associated with each instrument and connected to the signal transmitter associated with the respective instrument, and connected to the logic circuits associated with the other instruments, each logic circuit being operable to generate an actuation signal for the respective instrument and a blocking signal for supply to the other logic circuits when an extraction signal is transmitted in respect of the respective instrument and when no blocking signal is supplied by any of the other logic circuits;
a single connecting line connected to said logic circuits for transmitting blocking signals there between;
and a logic identification circuit associated with each logic circuit, each logic identification circuit being connected to said connecting line and to an input and to an output of the associated logic circuit, and each logic identification circuit being operable to transmit a blocking signal which may be present in the connecting line to the input of the associated logic circuit when an actuating signal is absent from the output of the logic circuit.

2. Dental apparatus according to claim 1, including one-way transmission means interconnecting the output of each logic circuit and the connecting line, said transmission means being operable to transmit only in the direction from said output to the connecting line.

3. Dental apparatus according to claim 2, in which each logic circuit comprises a NAND element having an input connected to the respective signal transmitter; each identification circuit comprises a further NAND element and an inverter having an input connected to said connecting line and an output connected to one of the inputs of said further NAND element; a further input of said further NAND element is connected to the output of the first-mentioned NAND element; the output of said further NAND element is connected to the other input of the first-mentioned NAND element; and said one-way transmission means is connected to the output of the first-mentioned NAND element.

4. Dental apparatus according to claim 2, in which said signal transmitters logic circuits and logic identification circuits are electrically operable, and in which each one-way transmission means comprises a diode.

* * * * *